US005345009A

United States Patent [19]
Sanderson et al.

[11] Patent Number: 5,345,009
[45] Date of Patent: Sep. 6, 1994

[54] CONJOINT PRODUCTION OF DITERTIARY BUTYL PEROXIDE AND TERTIARY BUTYL ALCOHOL FROM TERTIARY BUTYL HYDROPEROXIDE

[75] Inventors: John R. Sanderson, Leander; John F. Knifton, Austin, both of Tex.

[73] Assignee: Texaco Chemical Company, White Plains, N.Y.

[21] Appl. No.: 150,913

[22] Filed: Nov. 12, 1993

[51] Int. Cl.$^5$ .................. C07C 29/132; C07C 31/12
[52] U.S. Cl. .................. 568/909.8; 568/558; 568/840
[58] Field of Search ............ 568/558, 561, 715, 815, 568/840

[56] References Cited

U.S. PATENT DOCUMENTS

| | | | |
|---|---|---|---|
| 2,854,487 | 9/1958 | Quin | 568/909.8 |
| 3,474,151 | 10/1969 | Grane | 568/558 |
| 4,294,999 | 10/1981 | Grame et al. | 568/910 |
| 4,551,553 | 11/1985 | Tayler et al. | 568/909.8 |
| 4,705,903 | 11/1987 | Sanderson et al. | 568/922 |
| 4,810,809 | 3/1989 | Sanderson et al. | 568/909.8 |
| 4,900,850 | 2/1990 | Sanderson et al. | 568/909.8 |
| 5,025,113 | 6/1991 | Sanderson et al. | 568/909.8 |

*Primary Examiner*—Werren B. Lone
*Attorney, Agent, or Firm*—James L. Bailey; Kenneth R. Priem; Carl G. Ries

[57] ABSTRACT

A method for conjointly preparing tertiary butyl alcohol and ditertiary butyl peroxide wherein a solution of a tertiary butyl hydroperoxide feedstock in tertiary butyl alcohol is charged to a hydroperoxide decomposition reaction zone containing a catalytically effective amount of a hydroperoxide decomposition catalyst consisting essentially of palladium supported on pelleted carbon, and is brought into contact with the catalyst in liquid phase under hydroperoxide decomposition reaction conditions to convert the tertiary butyl hydroperoxide to decomposition products, principally tertiary butyl alcohol and ditertiary butyl peroxide.

3 Claims, No Drawings

CONJOINT PRODUCTION OF DITERTIARY BUTYL PEROXIDE AND TERTIARY BUTYL ALCOHOL FROM TERTIARY BUTYL HYDROPEROXIDE

BACKGROUND OF THE INVENTION

1. Field of the Invention

This invention relates to the conjoint production of tertiary butyl alcohol and ditertiary butyl peroxide from tertiary butyl hydroperoxide. More particularly, the invention relates to a continuous catalytic method for the conjoint production of tertiary butyl alcohol and ditertiary butyl peroxide from a solution of tertiary butyl hydroperoxide in tertiary butyl alcohol. Still more particularly, this invention relates to a continuous method for the conjoint production of tertiary butyl alcohol and ditertiary butyl peroxide by bringing a tertiary butyl alcohol solution of tertiary butyl hydroperoxide into contact with a pelleted carbon catalyst having palladium deposited thereon.

2. Prior Art

It is known to react isobutane with oxygen, either thermally or catalytically, to form a peroxidation reaction product wherein the principal peroxide that is formed is tertiary butyl hydroperoxide. It is also known to thermally or catalytically decompose the tertiary butyl hydroperoxide to form tertiary butyl alcohol. It is also known, as pointed out in Sanderson et al. U.S. Pat. Nos. 4,810,809 and 4,900,850 that ditertiary butyl peroxide is a minor constituent of the reaction product. Ditertiary butyl peroxide is a valuable commercial product used, for example, as a high temperature free radical initiator in chemical reactions. These two Sanderson et al. patents disclose methods that can be used to recover purified ditertiary butyl peroxide from a reaction product formed by the thermal or catalytic decomposition of tertiary butyl hydroperoxide.

In the text entitled "Organic Peroxides" edited by Daniel Swern (Wiley Interscience, a Division of John Wiley & Sons, New York), in Vol. II on page 157 it is stated that the metal-ion-catalyzed decomposition of primary hydroperoxides yields mainly alcohols, aldehydes and carboxylic acids, citing as an example the decomposition of hydroxymethyl hydroperoxide with aqueous ferrous sulfate to provide formaldehyde, formic acid and water.

Quin U.S. Pat. No. 2,854,487 discloses the hydrogenation of hydrocarbon peroxides in the presence of hydrogen and palladium on activated alumina to provide carbinols.

Grane U.S. Pat. No. 3,474,151 discloses that tertiary butyl alcohol starts to dehydrate at 450° F. and to decompose at a "rapid rate" at temperatures above 475° F. Grane discovered, however, that residual quantities of hydroperoxide contaminants present in tertiary butyl alcohol could be thermally decomposed by heating the contaminated tertiary butyl alcohol at a temperature of 375° to 475° F. for about 1 to 10 minutes.

Grane et al. U.S. Pat. No. 4,294,999 discloses a process wherein isobutane is oxidized in a pressured reactor in the presence of a solubilized molybdenum catalyst to provide a mixture of tertiary butyl alcohol, tertiary butyl hydroperoxide, methanol, acetone, and other oxygen-containing compounds. The tertiary butyl hydroperoxide is thermally decomposed under pressure at about 280° F. to provide a tertiary butyl alcohol product containing only residual quantities of tertiary butyl hydroperoxide which are then decomposed in accordance with Grane U.S. Pat. No. 3,474,151 by heating the tertiary butyl alcohol at 375° to 475° for about 1 to 10 minutes. Heating tertiary butyl alcohol containing small amounts of peroxides at high temperatures for even short periods of time to remove the peroxides produces undesirable products such as isobutylene.

Taylor et al. U.S. Pat. No. 4,551,553 is directed to a process for the formation of alcohols such as tertiary butyl alcohol by the catalytic decomposition of an organic hydroperoxide such as tertiary butyl hydroperoxide using a binary catalyst composed of a mixture of a ruthenium compound with a chromium compound. It is stated that the use of the binary catalyst eliminates the need for stabilizing ligands.

Sanderson et al. disclose the use of a variety of catalysts for the decomposition of tertiary butyl hydroperoxide in a series of U.S. patents, including a catalyst composed of unsupported nickel, copper, chromia and iron (U.S. Pat. No. 4,704,482), a catalyst composed of iron, copper, chromia and cobalt (U.S. Pat. No. 4,705,903), a catalyst composed of a base treated hydrogenation catalyst from groups VIB or VIIIB of the Periodic Table (U.S. Pat. No. 4,742,179), a catalyst consisting essentially of nickel, copper, chromium and barium (U.S. Pat. No. 4,873,380), a catalyst composed of a metal phthalocyanine promoted with a rhenium compound (U.S. Pat. No. 4,910,349), a catalyst composed of a base promoted metal phthalocyanine compound (U.S. Pat. No. 4,912,269), a catalyst composed of a soluble ruthenium compound promoted with a bidentate ligand (U.S. Pat. No. 4,912,033), a catalyst composed of a metal porphine such as iron (III) or manganese (III) promoted with an alkyl thiol or an amine, a catalyst composed of an imidazole promoted metal phthalocyanine compound (U.S. Pat. No. 4,912,266), (U.S. Pat. No. 4,922,034), a catalyst composed of a metal phthalocyanine promoted with a thiol and a free radical inhibitor (U.S. Pat. No. 4,922,035), a catalyst composed of a borate promoted metal phthalocyanine (U.S. Pat. No. 4,922,036), or a catalyst composed of a soluble ruthenium compound and an iron compound such as an acetate, a borate, a bromide, a chloride, a 1,3-propanedionate, a 2-ethyl-hexanoate, an iodide, a nitrate, a 2,4-pentanedionate, a perchlorate or a sulfate (U.S. Pat. No. 5,025,113).

BACKGROUND INFORMATION

When isobutane is reacted with molecular oxygen, the principal products of the reaction are tertiary butyl alcohol and tertiary butyl hydroperoxide. However, minor amounts of other oxygen-containing contaminants are also formed.

In addition, a minor amount of water will be formed, which will normally amount to about 0.5 to 1 wt. % of the reactor effluent. The amount of byproduct water that is produced is a function of the severity of the reaction conditions employed and will tend to increase as the severity of the reaction conditions is increased.

As indicated, tertiary butyl hydroperoxide is useful as a raw material for the manufacture of tertiary butyl alcohol and ditertiary butyl peroxide.

SUMMARY OF THE INVENTION

It has been discovered in accordance with the present invention that tertiary butyl alcohol and an enhanced amount of ditertiary butyl peroxide are formed when a solution of tertiary butyl hydroperoxide in tertiary butyl alcohol is brought into contact with a catalytically effective Mount of a catalyst consisting essentially of pelleted carbon having palladium deposited thereon. Tertiary butyl alcohol and ditertiary butyl peroxide can be recovered from the products of the reaction.

DESCRIPTION OF THE PROCESS OF THE PRESENT INVENTION

The starting materials for the process of the present invention are a tertiary butyl hydroperoxide feedstock and a carbon supported palladium catalyst.

The Tertiary Butyl Hydroperoxide Feedstock

The tertiary butyl hydroperoxide charge stock may comprise an isobutane oxidation product wherein the tertiary butyl hydroperoxide is dissolved in a mixture of isobutane and tertiary butyl alcohol or may comprise an isobutane oxidation product enriched by the addition of tertiary butyl alcohol, such that the solution of tertiary butyl alcohol in the mixture of isobutane with tertiary butyl alcohol contains from about 5 to about 30 wt. % of tertiary butyl hydroperoxide.

Alternately, the isobutane reaction product may be charged to a distillation zone where unreacted isobutane is removed as a distillate fraction for recycle to thereby provide a solution of tertiary butyl hydroperoxide in tertiary butyl alcohol containing about 5 to about 30 wt. % of tertiary butyl hydroperoxide.

The Catalyst

The catalyst to be used in accordance with the present invention is a hydroperoxide decomposition catalyst consisting essentially of carbon-supported palladium, such as pelleted carbon having from about 0.1 to about 1 wt. % of palladium deposited thereon.

Catalytic Decomposition of Tertiary Butyl Hydroperoxide

The process of the present invention may be conducted batchwise in kettles or by continuously passing the reactants through a tubular reactor.

The catalytic decomposition of the tertiary butyl hydroperoxide is preferably conducted at a temperature within the range of about 20° to about 160° C. and, more preferably, at a temperature within the range of about 80° to about 100° C. The reaction is preferably conducted at a pressure sufficient to keep the reactants and the reaction products in liquid phase. A pressure of about 0 to about 10,000 psig. may be used, if desired.

Flow rates of the charge solution to the reaction zone should be adjusted in order to provide an appropriate contact time within the reactor. In a batch process, the holding time may suitably be from about 0.5 to about 10 hours, and more preferably about 1 to 3 hours.

In accordance with a preferred embodiment of the present invention, isobutane is reacted with oxygen in an oxidation zone under oxidation reaction conditions including a temperature of about 135° to about 155° C., a pressure of about 300 to about 800 psig., and a holding time of about 2 to about 6 hours to provide an initial oxidation reaction product comprising unreacted isobutane, tertiary butyl hydroperoxide, tertiary butyl alcohol, and oxygen-containing by-products. The initial oxidation reaction product is then used as the tertiary butyl hydroperoxide charge stock of the present invention. If the concentration of tertiary butyl hydroperoxide in the tertiary butyl hydroperoxide charge stock is more than about 30 wt. % of the initial oxidation reaction product, the initial oxidation reaction product can be diluted with an amount of tertiary butyl alcohol sufficient to lower the concentration of the tertiary butyl hydroperoxide to a desired percentage, to provide, for example, a tertiary butyl hydroperoxide charge stock containing from about 15 to about 25 wt. % of tertiary butyl hydroperoxide.

Alternately, the initial oxidation reaction product may be fractionated in any appropriate manner (e.g., by distillation in a distillation zone) to remove the isobutane therefrom for recycle and to provide a solution of tertiary butyl hydroperoxide and tertiary butyl alcohol which will normally contain from about 5 to about 30 wt. % of tertiary butyl hydroperoxide.

The solution of tertiary butyl hydroperoxide in tertiary butyl alcohol is then charged to a catalytic hydroperoxide decomposition zone where it is brought into contact with an a carbon-supported palladium catalyst to conjointly convert the tertiary butyl hydroperoxide to tertiary butyl alcohol and ditertiary butyl peroxide with high yields and selectivities.

As indicated, the catalytic decomposition of the tertiary butyl hydroperoxide in the catalytic hydroperoxide decomposition reaction zone may suitably be conducted at a temperature within the range of about 40° to about 160° C., preferably from about 60° to about 120° C., and more preferably from about 80° to 100° C. at autogenous pressure or if desired at a superatmospheric pressure up to 10,000 psig. for a contact time within the range of about 0.5 to about 10 hours, and more preferably about 1 to 3 hours.

When the process of the present invention is practiced in a continuous manner by continuously charging the tertiary butyl hydroperoxide charge stock to a reactor containing a fixed bed of pelleted hydroperoxide decomposition catalyst, the space velocity is suitably in the range of about 0.5 to about 3 volumes of tertiary butyl hydroperoxide charge stock per volume of catalyst per hour. Preferably, the space velocity is within the range of about 1 to about 2 volumes of tertiary butyl hydroperoxide charge stock per volume of catalyst per hour.

The reaction product from the tertiary butyl hydroperoxide decomposition step may then be fractionated in any suitable manner, such as by distillation to recover the tertiary butyl alcohol.

SPECIFIC EXAMPLES

The invention will be further illustrated by the following specific examples which are given by way of illustration and not as limitations on the scope of this invention.

Procedure

A 20 wt. % solution of tertiary butyl hydroperoxide in tertiary butyl alcohol was used as the reactor feed. Analysis of the reactor effluent was by GC. Details are given in the following tables.

EXAMPLE 1

Reactor

The reactor was a stainless steel tube (0.51"×29") which was electrically heated. Liquid feed was pumped into the bottom of the reactor. Pressure regulation was with a Skinner Uni-Flow valve and a Foxboro controller. The liquid feed was pumped with a Ruska dual drive pump.

In this example, the catalyst consisted essentially of palladium supported on pelleted carbon.

A palladium on carbon catalyst gave conversion of TBHP similar to the palladium on alumina catalysts, but the selectivity to DTBP was much higher-especially at lower temperatures. For example, at 80° C. (0.5 space velocity), a 79.1% conversion of TBHP was observed with a selectivity to TBA on 73.5% and a selectivity to DTBP of 21.5%. Under the same conditions, but with a Pd/Pt on alumina catalyst, at 74.2% conversion of TBHP was observed with selectivity to TBA of 84.1% and DTBP of 5.0%.

TABLE 1

CATALYTIC CONVERSION OF TERT-BUTYLHYDROPEROXIDE TO TERT-BUTYLALCOHOL AND DITERTIARY BUTYL PEROXIDE

| Notebook Number | 6952-39-G | 7012-22-1 | 7012-22-2 | 7012-22-3 | 7012-22-4 |
|---|---|---|---|---|---|
| Catalyst | | .8% Pd on Carbon | | | |
| Catalyst (cc) | | 100 | 100 | 100 | 100 |
| Pressure (psig) | | 300 | 300 | 300 | 300 |
| Feed Rate (cc/Hr.) | | 50 | 50 | 50 | 50 |
| Temperature (°C.) | | 60 | 80 | 100 | 120 |
| Time on Stream (Hr) | | 4 | 4 | 4 | 4 |
| Space Vel. (cc/cc) | | 0.5 | 0.5 | 0.5 | 0.5 |
| TBHP Conversion (mol. %) | | 79.1 | 74.2 | 94.3 | 99.8 |
| Selectivity IC4= (mol. %) | | 0.1 | 0.2 | 0.9 | 23.7 |
| Sel. Acetone (mol. %) | | 5.0 | 7.1 | 10.0 | 15.3 |
| Sel. Methanol (mol. %) | | 0.9 | 2.3 | 3.3 | 3.4 |
| Sel. TBA (mol. %) | | 73.5 | 75.8 | 79.6 | 78.4 |
| Sel. DTBP (mol. %) | | 21.5 | 17.1 | 10.4 | 6.4 |
| Composition, wt % | | | | | |
| IC4= | 0.000 | 0.006 | 0.018 | 0.110 | 3.012 |
| MEOH/MF | 0.005 | 0.058 | 0.130 | 0.234 | 0.254 |
| Acetone | 0.013 | 0.534 | 0.711 | 1.265 | 2.027 |
| TBA | 78.494 | 90.807 | 89.375 | 92.484 | 90.374 |
| DTBP | 0.049 | 2.879 | 2.157 | 1.674 | 1.108 |
| TBHP | 20.512 | 4.293 | 5.289 | 1.169 | 0.041 |

TABLE 2

CATALYTIC CONVERSION OF TERT-BUTYLHYDROPEROXIDE TO TERT-BUTYLALCOHOL AND DITERTIARY BUTYL PEROXIDE

| Notebook Number | 6952-39-G | 7012-23-1 | 7012-23-2 | 7012-23-3 | 7012-23-4 |
|---|---|---|---|---|---|
| Catalyst | | .8% Pd on Carbon | | | |
| Catalyst (cc) | | 100 | 100 | 100 | 100 |
| Pressure (psig) | | 300 | 300 | 300 | 300 |
| Feed Rate (cc/Hr.) | | 100 | 100 | 100 | 100 |
| Temperature (°C.) | | 60 | 80 | 100 | 120 |
| Time on Stream (Hr) | | 4 | 4 | 4 | 4 |
| Space Vel. (cc/cc) | | 1.0 | 1.0 | 1.0 | 1.0 |
| TBHP Conversion (mol. %) | | 11.7 | 53.6 | 79.2 | 98.8 |
| Selectivity IC4= (mol. %) | | 0.7 | 0.6 | 1.3 | 14.3 |
| Sel. Acetone (mol. %) | | 8.0 | 8.0 | 11.2 | 21.0 |
| Sel. Methanol (mol. %) | | 2.0 | 2.0 | 4.2 | 5.3 |
| Sel. TBA (mol. %) | | 68.7 | 73.6 | 77.1 | 74.5 |
| Sel. DTBP (mol. %) | | 23.3 | 18.4 | 11.7 | 4.5 |
| Composition, wt % | | | | | |
| IC4= | 0.000 | 0.010 | 0.038 | 0.129 | 1.806 |
| MEOH/MF | 0.005 | 0.022 | 0.083 | 0.250 | 0.384 |
| Acetone | 0.013 | 0.137 | 0.580 | 1.182 | 2.761 |
| TBA | 78.494 | 80.143 | 86.288 | 89.745 | 91.426 |
| DTBP | 0.049 | 0.500 | 1.692 | 1.589 | 0.785 |
| TBHP | 20.512 | 18.119 | 9.509 | 4.273 | 0.241 |

TABLE 2

CATALYTIC CONVERSION OF TERT-BUTYLHYDROPEROXIDE TO TERT-BUTYLALCOHOL AND DITERTIARY BUTYL PEROXIDE

| Notebook Number | 6952-39-G | 7012-24-1 | 7012-24-2 | 7012-24-3 | 7012-24-4 |
|---|---|---|---|---|---|
| Catalyst | | .8% Pd on Carbon | | | |
| Catalyst (cc) | | 100 | 100 | 100 | 100 |
| Pressure (psig) | | 300 | 300 | 300 | 300 |
| Feed Rate (cc/Hr.) | | 200 | 200 | 200 | 200 |
| Temperature (°C.) | | 60 | 80 | 100 | 120 |
| Time on Stream (Hr) | | 4 | 4 | 4 | 4 |
| Space Vel. (cc/cc) | | 2.0 | 2.0 | 2.0 | 2.0 |
| TBHP Conversion (mol. %) | | 5.2 | 12.0 | 40.3 | 96.5 |
| Selectivity IC4= (mol. %) | | n.d. | 0.7 | 1.2 | 22.1 |
| Sel. Acetone (mol. %) | | n.d. | 9.6 | 10.9 | 21.7 |
| Sel. Methanol (mol. %) | | n.d. | 2.5 | 3.5 | 6.5 |
| Sel. TBA (mol. %) | | n.d. | 72.3 | 75.2 | 73.4 |
| Sel. DTBP (mol. %) | | n.d. | 18.1 | 13.9 | 5.0 |
| Composition, wt % | | | | | |

TABLE 2-continued

CATALYTIC CONVERSION OF TERT-BUTYLHYDROPEROXIDE
TO TERT-BUTYLALCOHOL AND DITERTIARY BUTYL PEROXIDE

| Notebook Number | 6952-39-G | 7012-24-1 | 7012-24-2 | 7012-24-3 | 7012-24-4 |
|---|---|---|---|---|---|
| IC4= | 0.000 | 0.018 | 0.011 | 0.060 | 2.721 |
| MEOH/MF | 0.005 | 0.021 | 0.027 | 0.107 | 0.465 |
| Acetone | 0.013 | 0.110 | 0.165 | 0.595 | 2.778 |
| TBA | 78.494 | 79.222 | 80.216 | 84.312 | 89.631 |
| DTBP | 0.049 | 0.141 | 1.410 | 1.980 | 0.845 |
| TBHP | 20.512 | 19.454 | 18.051 | 12.251 | 0.709 |

Having thus described our invention, what is claimed is:

1. In a method wherein a tertiary butyl hydroperoxide charge stock comprising a solution of tertiary butyl hydroperoxide in tertiary butyl alcohol is brought into contact with a catalytically effective amount of a hydroperoxide decomposition catalyst in a hydroperoxide decomposition reaction zone in liquid phase to conjointly convert said tertiary butyl hydroperoxide to decomposition products, principally tertiary butyl alcohol, and ditertiary butyl peroxide, the improvement which comprises:
   a) using, as said hydroperoxide decomposition catalyst, palladium supported on pelleted carbon and
   b) recovering tertiary butyl alcohol and ditertiary butyl peroxide from the products of said hydroperoxide decomposition reaction.

2. In a method wherein a solution of a tertiary butyl hydroperoxide charge stock in tertiary butyl alcohol that contains from about 5 to about 30 wt. % of tertiary butyl hydroperoxide is brought into contact with a catalytically effective amount of a hydroperoxide decomposition catalyst in a hydroperoxide decomposition reaction zone in liquid phase under hydroperoxide conversion conditions including a temperature within the range of about 40° to about 160° C. and a pressure of about 0 to about 10,000 psig to convert said tertiary butyl hydroperoxide to decomposition products, principally tertiary butyl alcohol and ditertiary butyl peroxide, the improvement which comprises:
   a) using, as said hydroperoxide decomposition catalyst, a catalyst consisting essentially of about 0.1 to about 1 wt. % of palladium supported on pelleted carbon, and
   b) recovering tertiary butyl alcohol and ditertiary butyl peroxide from the products of said hydroperoxide decomposition reaction.

3. A method as in claim 2 wherein the temperature is in the range of about 60° to about 100° C., the pressure is about 0 psig.

* * * * *